United States Patent [19]

Ishihara et al.

[11] 4,384,158
[45] May 17, 1983

[54] METHOD FOR THE PREPARATION OF CIS-11-HEXADECEN-1-YNE

[75] Inventors: Toshinobu Ishihara; Akira Yamamoto; Kenichi Taguchi, all of Joetsu, Japan

[73] Assignee: Shin-Etsu Chemical Co., Ltd., Tokyo, Japan

[21] Appl. No.: 283,298

[22] Filed: Jul. 14, 1981

[30] Foreign Application Priority Data

Jul. 21, 1980 [JP] Japan .................................. 55-99598

[51] Int. Cl.$^3$ ................................................ C07C 2/00
[52] U.S. Cl. ...................................... 585/534; 585/505
[58] Field of Search ................................ 585/534, 505

[56] References Cited

U.S. PATENT DOCUMENTS 4,317,905  3/1982  Massardo et al. ................... 585/534

FOREIGN PATENT DOCUMENTS 377802   7/1964  Fed. Rep. of Germany ....... 585/534
42-13921 7/1967  Japan .................................. 585/534

OTHER PUBLICATIONS

Campbell et al., J. Am. Chem. Soc., 62, 1798 (1940).
Friedman et al., J. Am. Chem. Soc., 96, 7101 (1974).
J. March, Advanced Organic Chemistry, McGraw Hill, (1977), pp. 410–411.

Primary Examiner—Delbert E. Gantz
Assistant Examiner—A. Pal
Attorney, Agent, or Firm—Toren, McGeady and Stanger

[57] ABSTRACT

The invention provides a novel synthetic method for the preparation of an alkyne-1 compound of the general formula $R(CH_2)_nC\equiv CH$, in which R is a monovalent hydrocarbon group and n is an integer of 4, 5 or 6, which compound is useful as an intermediate of various organic compounds or, in particular, of several sexual pheromone of noxious insects expected to give a promising means for the extermination of the insects. The method comprises reacting an $\omega$-bromo-1-alkyne compound of the formula $Br(CH_2)_nC\equiv CH$, e.g. 8-bromo-1-octyne, with a Grignard reagent of the formula RMgX, e.g. cis-3-octenylmagnesium chloride, in tetrahydrofuran, preferably, in the presence of a catalyst which is dilithium copper tetrachloride or lithium copper dichloride.

3 Claims, No Drawings

METHOD FOR THE PREPARATION OF CIS-11-HEXADECEN-1-YNE

BACKGROUND OF THE INVENTION

The present invention relates to a method for the synthetic preparation of an alkyne-1 compound represented by the general formula $$R(CH_2)_nC\equiv CH, \quad (I)$$

in which R is a monovalent hydrocarbon group and n is an integer of 4, 5 or 6, or, in particular, of cis-11-hexadecen-1-yne.

The above described alkyne-1 compounds are known as a useful intermediate compound for the synthesis of several kinds of so-called sexual pheromone compounds of insects expected to provide a promising means for the extermination of noxious insects in the fields. For example, an industrially advantageous synthetic route with a high yield can be obtained by use of such an intermediate for the preparation of cis,cis-3,13-octadecadienyl acetate known as a sexual pheromone compound of a noxious insect momonokosukashiba but hardly obtained by any hitherto known synthetic method.

Accordingly, there has been eagerly desired to develop an industrially feasible method for the synthetic preparation of such alkyne-1 compounds.

SUMMARY OF THE INVENTION

Thus, it is an object of the present invention to provide a novel and improved method for the synthetic preparation of an alkyne-1 compound represented by the above given general formula (I) and the inventive method established as a result of the extensive investigations undertaken by the inventors comprises the coupling reaction of a Grignard reagent represented by the general formula $$RMgX, \quad (II)$$

in which R is a monovalent hydrocarbon group as mentioned above and X is a halogen atom, and an ω-bromoalkyne-1 compound represented by the general formula $$Br(CH_2)_nC\equiv CH, \quad (III)$$

in which n is an integer of 4, 5 or 6 as described above.

The above coupling reaction is most advantageously carried out in a medium of tetrahydrofuran in the presence of dilithium copper tetrachloride and/or lithium copper dichloride as a catalyst.

DETAILED DESCRIPTION OF THE PREFERRED EMBODIMENTS

One of the starting reactants in the above mentioned coupling reaction is the Grignard reagent of the general formula (II), in which the group denoted by R is a monovalent hydrocarbon group exemplified by alkyl groups such as ethyl, propyl and butyl groups, alkenyl groups such as vinyl, cis-3-octenyl and trans-3-octenyl groups, aryl groups such as phenyl group and alkynyl groups such as propargyl group. Such a Grignard reagent can readily be obtained by a conventional method of reacting a corresponding halogenated hydrocarbon with metallic magnesium in a suitable organic solvent such as tetrahydrofuran.

The other reactant to be reacted with the above mentioned Grignard reagent is the ω-bromoalkyne-1 compound of the general formula (III) with the integer n equal to 4, 5 or 6. This compound is also readily prepared by the reaction of a corresponding α,ω-dibromoalkane and sodium acetylide according to the equation $$Br(CH_2)_nBr + NaC\equiv CH \rightarrow Br(CH_2)_nC\equiv CH + NaBr,$$

in which n has the same meaning as defined above.

The coupling reaction of the inventive method according to the equation $$RMgX + Br(CH_2)_nC\equiv CH \rightarrow R(CH_2)_nC\equiv CH + MgXBr,$$

in which R, X and n each have the same meaning as defined above, is advantageously carried out by adding dropwise a tetrahydrofuran solution of the Grignard reagent prepared in a conventional manner into the reaction mixture of the ω-bromoalkyne-1 compound dissolved in tetrahydrofuran and a catalyst contained in a reaction vessel.

The molar ratio of the reactants should be preferably such that from 0.5 to 1.5 moles of the ω-bromoalkyne-1 compound is taken in the reaction vessel per mole of the Grignard reagent. The reaction mixture should be kept at a temperature in the range from −20° to 30° C. or, preferably, from −5° to 10° C. The coupling reaction is promoted by several catalysts, among which the most preferred is a lithium copper chloride such as dilithium copper tetrachloride and lithium copper dichloride. These catalyst compounds are added, either alone or as a combination of the two, to the reaction mixture in an amount from 0.5 to 2 g per mole of the Grignard reagent.

In the following, the method of the present invention is described in further detail by way of an example.

EXAMPLE

Into a flask of 500 ml capacity were taken 37.8 g (0.2 mole) of 8-bromo-1-octyne, 200 ml of tetrahydrofuran and 0.2 g of dilithium copper tetrachloride and the reaction mixture was chilled to 0° C. Into the reaction mixture under agitation were added dropwise 200 ml of a tetrahydrofuran solution of a Grignard reagent prepared separately from 29.4 g (0.2 mole) of cis-3-octene-1 chloride separately in advance, i.e. cis-3-octenylmagnesium chloride, to effect the coupling reaction.

After completion of the reaction followed by filtration of the reaction mixture, the solvent, i.e. tetrahydrofuran, was stripped off from the filtrate solution and the residue was subjected to distillation uner reduced pressure to give 26.4 g (0.12 mole) of cis-11-hexadecen-1-yne. The yield of the product was about 60% of the theoretical value.

What is claimed is:

1. A method for the preparation of cis-11-hexadecen-1-yne which comprises reacting 8-bromo-1-octyne and cis-3-octenylmagnesium chloride.

2. The method as claimed in claim 1 wherein the reaction of 8-bromo-1-octyne and cis-3-octenylmagnesium chloride is carried out in tetrahydrofuran in the presence of a catalyst selected from the class consisting of dilithium copper tetrachloride and lithium copper dichloride.

3. The method as claimed in claim 1 wherein the reaction of 8-bromo-1-octyne and cis-3-octenylmagnesium chloride is carried out at a temperature in the range from −5° C. to 10° C.

* * * * *